United States Patent [19]

Al-Muddarris

[11] 4,329,516

[45] May 11, 1982

[54] PROCESS FOR THE PRODUCTION OF METHYL T-BUTYL ETHER

[75] Inventor: Ghazi R. Al-Muddarris, Cologne, Fed. Rep. of Germany

[73] Assignee: Davy International Aktiengesellschaft, Fed. Rep. of Germany

[21] Appl. No.: 156,040

[22] Filed: Jun. 3, 1980

[30] Foreign Application Priority Data

May 28, 1979 [DE] Fed. Rep. of Germany ....... 2921576

[51] Int. Cl.$^3$ .............................................. C07C 41/05
[52] U.S. Cl. .................................... 568/697; 568/699; 585/331; 585/332; 585/660; 585/661; 585/734; 585/738; 585/654
[58] Field of Search ................ 568/697, 699; 585/654, 585/660, 661, 331, 332, 734, 738

[56] References Cited

U.S. PATENT DOCUMENTS

| | | | |
|---|---|---|---|
| 2,393,041 | 1/1946 | Greensfelder | 585/734 |
| 2,396,853 | 3/1946 | Jones | 585/734 |
| 3,531,266 | 9/1970 | Chernoff | 260/449.5 |
| 3,726,942 | 4/1973 | Louder | 568/697 |
| 3,755,480 | 8/1973 | Wilhelm | 585/660 |
| 3,912,463 | 10/1975 | Kozlowski et al. | 568/697 UX |
| 4,118,425 | 10/1978 | Herbstman | 568/697 |
| 4,198,530 | 4/1980 | Wentzheimer et al. | 568/697 |
| 4,219,678 | 8/1980 | Obenaus et al. | 568/697 |

*Primary Examiner*—Howard T. Mars
*Attorney, Agent, or Firm*—Bernard, Rothwell & Brown

[57] ABSTRACT

A process is described for producing methyl tert.-butyl ether from butane-containing light hydrocarbon mixtures. The n-butane is isomerized to isobutane which is dehydrogenated to an isobutene/isobutane molar ratio of 0.4 to 2:1, the isobutene in the mixture is etherified with methanol to form methyl tert.-butyl ether and the residual isobutane is recycled for dehydrogenation. After the isomerization step, the n-butane and isobutane can be separated and the n-butane recycled. The product containing methyl tert.-butyl ether can be used as a gasoline additive.

8 Claims, 1 Drawing Figure

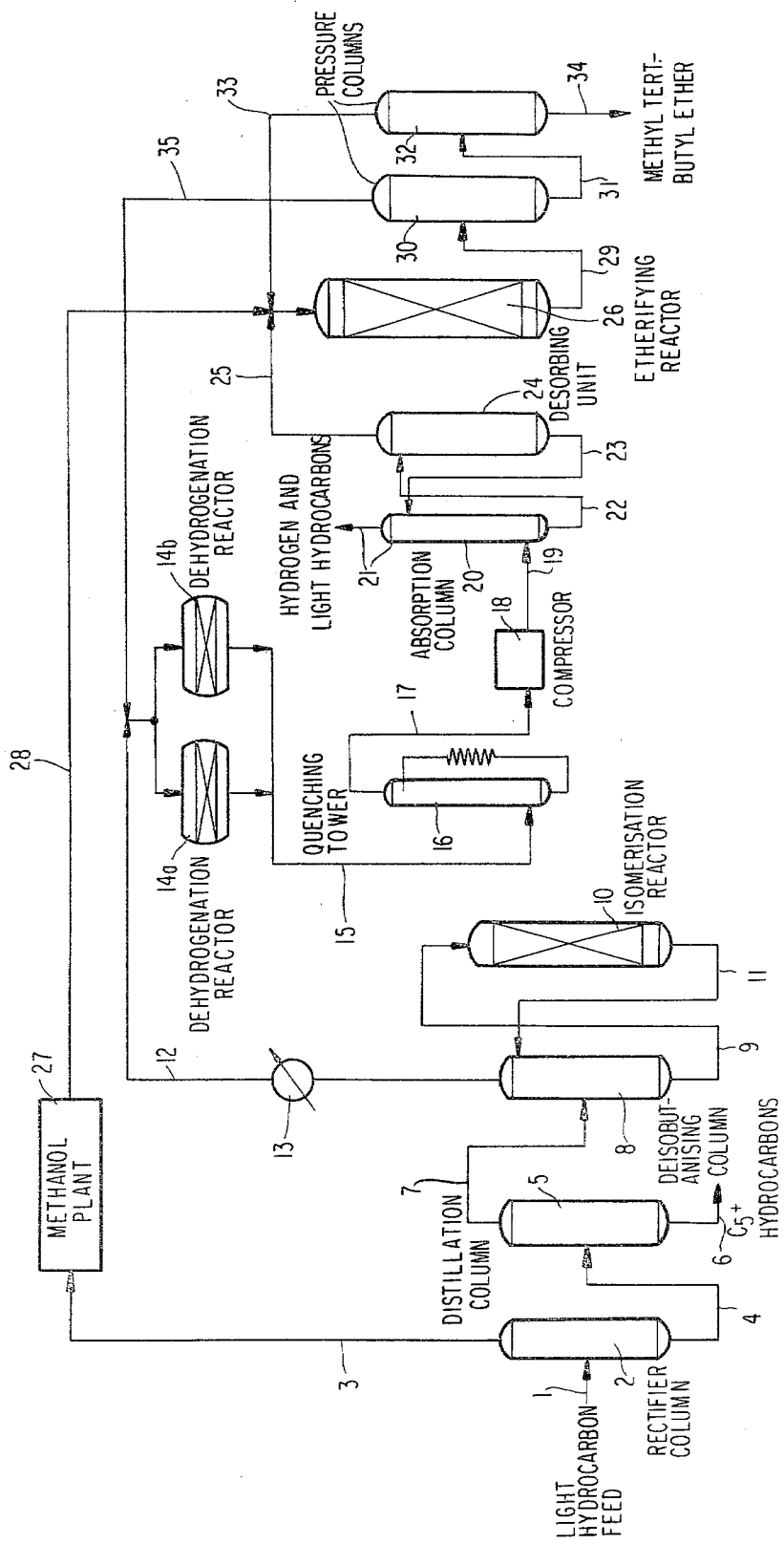

PROCESS FOR THE PRODUCTION OF METHYL T-BUTYL ETHER

The invention relates to a process for the production of methyl tert.-butyl ether from a mixture of light hydrocarbons which contain butane or butanes.

In the petroleum-exporting countries, considerable quantities of gaseous paraffin hydrocarbons are formed during the refining of the crude oil by distillation. Frequently, no possibility exists for the exploitation of these products on the spot. Since the transportation of butane to the consuming countries is costly and has so far not been done on a relatively large scale, at the present time considerable quantitites of butane are burnt off.

It is known from German Offenlegungsschrift No. 26 20 011 to process a stream of n-butane formed in the petroleum refinery into methyl tert.-butyl ether. In accordance therewith, the n-butane is partially isomerised to form isobutane, the resulting n-butane/isobutane mixture is partially dehydrogenated, with n-butenes being formed as well as isobutene. The dehydrogenation product, still containing n-butane, is then etherified with excess alcohol, more especially with methanol, the isobutene formed in the dehydrogenation stage being converted to methyl tert.-butyl ether. The excess methanol is removed from the product mixture by extraction with water, and the remaining $C_4$ hydrocarbons are separated from the ether by distillation and returned into the dehydrogenation stage. Due to the presence of n-butane, which is necessary with this process, it is necessary to have correspondingly relatively large dimensions of the installation for a given production output. Moreover, due to the presence of n-butane, butadiene is also formed in the dehydrogenation stage, especially when $C_4$ hydrocarbons which contain n-butene are recycled. This is undesirable, since butadiene has a tendency to form a resin. Finally, the separation of methanol from the etherified mixture by extraction with water is also disadvantageous, because thereafter both a methanol/water separation and also drying of the ether are necessary.

The present invention seeks to convert the butane fraction of the light hydrocarbons being liberated with the refining of petroleum oil into methyl tert.-butyl ether and in this way to transform this fraction, which in many cases can only be exploited with difficulty, into a high-quality gasoline additive. The transporting of such a product to the petroleum-importing countries is substantially more economical than the transporting of butane. As a further objective of the present invention, the conversion of the n-butane into the high-octane methyl tert.-butyl ether is to be carried out substantially completely, and the formation of butadiene is to be largely avoided.

The invention accordingly provides an improvement of a process for the production of methyl tert.-butyl ether from a mixture of light hydrocarbons which contain butane or butanes. Such a process involves separation of the butane fraction from the light hydrocarbon mixture, isomerisation of n-butane to form isobutane, dehydrogenation of the isobutane down to an isobutene/isobutane molar ratio in the range from 0.4 to 2:1, advantageously 1.0 to 1.5:1, etherification of the isobutene contained in the dehydrogenation mixture with methanol, with formation of methyl tert.-butyl ether, separation of the isobutane from the etherification mixture and recycle of the isobutane to the dehydrogenation stage.

According to the present invention, the improvement of this process comprises the steps of: (a) separating the butane fraction after isomerisation of the n-butane therein into an n-butane fraction and an isobutane fraction by means of distillation; (b) recycling the resulting n-butane fraction to the isomerisation step; (c) dehydrogenating the resulting isobutane fraction which, together with whatever isobutane has been recycled from the etherification mixture, has an isobutane content of from about 70% to 100%, preferably about 90% to 99%, by weight, to thereby form the dehydrogenation mixture; (d) separating from the resulting dehydrogenation mixture a mixture consisting essentially of isobutane and isobutene, by means of absorption and desorption separation techniques, which separated isobutene/isobutane mixture is thereafter reacted with methanol to form the etherification product containing methyl tert.-butyl ether and isobutane; and (e) thereafter separating substantially all of the isobutane from the etherification product by distillation, which isobutane is recycled to the dehydrogenation step and preferably also separating unreacted methanol from the etherification product by distillation.

In the case where the gases are liberated with the working up of a crude petroleum by distillation, the butane-containing mixture of light hydrocarbons consists, for example, of 5% by volume methane, 10% by volume ethane, 30% by volume propane, 35% by volume butanes and 20% by volume pentanes and higher hydrocarbons. The butane fraction can be separated by intense cooling or other known measures from the crude oil distillation waste gas. Obviously, the butane fraction used in the process according to the invention can also contain butenes, if the basic hydrocarbon mixture comprises cracking gases or other olefin-containing refinery gases.

The isomerisation of the n-butane is expediently carried out on a platinum-containing solid bed catalyst in the presence of hydrogen in a temperature range from 150° to 205° C., advantageously 150° to 180° C. The operation takes place at superatmospheric pressure, advantageously in the pressure range from 14 to 28 atmospheres. The isomerisation product which is obtained consists, for the major part, advantageously of 55 to 60% of isobutane and, for the remainder, substantially of n-butane. The isomerisation conditions, i.e. temperature, space velocity and pressure, are so adjusted that an extensive approximation to the isomerisation equilibrium is provided. The product consisting of isobutane and n-butane can then be rectified together with the butane fraction used in the process, which fraction may likewise be a mixture of n-butane and isobutane and possibly butenes. The separation of these two streams or flows into an isobutane stream and an n-butane stream can be effected, for example, in a column having about 50 to 100 plates at pressures in the range from about 8 to 14 atmospheres, advantageously about 9 to 12 atmospheres, and temperatures in the range from about 60° to 90° C., advantageously about 70° to 80° C. While the n-butane fraction is supplied to the isomerisation stage, the isobutane fraction passing out at the top is combined with the isobutane separated from the etherification product. The combined isobutane stream has an isobutane content of at least about 70 and advantageously at least about 90% by weight, the remainder consisting essentially of n-butane and possibly butenes. Preferably, the isobutane content of the stream supplied to the dehydrogenation stage is higher than about 95% by weight.

The dehydrogenation of the isobutane can be effected by either strictly thermal or by catalytic procedures. Dehydrogenation can advantageously be effected catalytically by a solid bed process in several reactors, which are alternately charged with the isobutane stream. The dehydrogenation temperature is in the range from about 538° to 649° C. and the pressure is preferably in the range from about 0.2 to 0.9 atmosphere absolute. The dehydrogenation catalyst generally consists of active aluminium oxide, which is impregnated with 18 to 20% chromium oxide and has the form of cylindrical pellets. The heat of reaction is mainly supplied by the heat of combustion of a small quantity of coke, which is deposited during the reaction period on the catalyst. This coke is burnt in the regeneration periods, as a result of which a rise in temperature occurs in the reactor. Furthermore, the stream of isobutane is preheated before being introduced into the reactor, so that it vaporises spontaneously with the expansion to the reaction pressure. In the process according to the present invention, the isobutane, depending on the operating conditions in the reactor, can be more or less largely dehydrogenated to isobutene. The isobutene/isobutane ratio in the exhaust stream of the reactor is advantageously in the range from 1.0 to 1.5. The proportion of the secondary products, as for example propane, is small. The exhaust flow from the dehydrogenation reactor is generally cooled by contact with cold oil, compressed to a pressure in the range from about 8 to 15 atmospheres with intermediate cooling, in which case a part of the $C_4$ fraction already condenses. The uncondensed gases are absorbed with absorption oil for the purpose of recovering isobutane/isobutene. The residual gases can be used in the production of the methanol required for the following etherification stage. After desorption of the $C_4$ hydrocarbons from the absorption oil and being united with the condensed $C_4$ hydrocarbons from the compression stage, propane can be separated out in a stabilisation column. The $C_4$ hydrocarbons as thus obtained consist essentially only of isobutane and isobutene. They are more especially free from butenes and butadiene.

The isobutane/isobutene mixture is then catalytically etherified with methanol, the isobutene being almost quantitatively converted to methyl tert.-butyl ether, while the isobutane experiences no conversion and leaves the reactor unchanged. Catalysts for etherification can include, for example, sulphonated ion exchange resins arranged as a solid bed, such as those which have frequently been described for this reaction, for example, in the German Offenlegungsschrift No. 26 20 011 already mentioned. Generally, the etherification takes place in the liquid phase at temperatures in the range from about 30° to 100° C., advantageously about 60° to 90° C. and pressures from about 2 to 24 and advantageously about 10 to 22 atmospheres. The pressure only serves the purpose of keeping the components in the reaction mixture in liquid phase during the reaction. The molar ratio of methanol to isobutene is generally maintained in the range from about 1 to 2:1, advantageously in the range from about 1.1 to 1.4:1.

The exhaust flow from the etherification reactor consists essentially of methyl tert.-butyl ether, isobutane and excess methanol. It is an essential advantage of the process according to the invention that the isobutane, and also the methanol, are capable of being easily separated from the etherification mixture and used again in the process. For this purpose, the product mixture discharging from the etherification reactor is supplied to a pressure distillation column, in which the isobutane is distilled off at the top, while the methanol/ether mixture is extracted from the sump. The isobutane is combined with the top or head product coming from the separation column of the isomerisation stage and then recycled to the dehydrogenation stage. The ether/methanol mixture is distilled in a second pressure distillation column, an ether/methanol azeotrope with a composition dependent on the distillation pressure passing out at the top and pure methyl tert.-butyl ether remaining in the sump. The azeotrope can be returned into the etherification stage. With this separation of the methanol from the etherification product, it is not essential to distill down to pure methyl tert.-butyl ether. If desired, a small proportion, for example, up to 10% by volume, of methanol can remain in the ether. The operational costs for the return of the azeotrope are thereby reduced. If the isobutene has been etherified only with a small methanol excess, the methanol separation may be completely omitted.

The dehydrogenation is advantageously operated with a charge having such a composition and under such reaction conditions that the butadiene content of the dehydrogenation mixture remains below 0.5% by weight. Due to the fact that the charge in the dehydrogenation stage is substantially free from n-butane and n-butenes, the formation of butadiene remains small. A selective hydrogenation of the dehydrogenation mixture for the purpose of removing butadiene is consequently unnecessary.

According to a preferred embodiment of the process according to the invention, the isobutene/isobutane mixture is etherified with methanol, which has been produced by reforming light hydrocarbons with steam and catalytic synthesis under a pressure in the range from about 40 to 100 atmospheres. Consequently, the same mixture of light hydrocarbons, from which the isobutene/isobutane mixture for the etherification has been obtained, is used as starting material for the methanol synthesis. The same mixture is expediently used for the methanol synthesis, after the butane fraction for the production of the isobutene/isobutane mixture has been separated out.

Hydrogen is expediently separated from the product gas of the dehydrogenation and/or the process gas and/or the exhaust gas of the methanol synthesis, and this hydrogen is used with the isomerisation and possibly other hydrogenconsuming processes. The separation of the hydrogen from the accompanying gases, more especially the light hydrocarbons, can for example be effected by adsorption or by low-temperature cooling and condensation of the accompanying gases. The hydrogen which is thus available can be used more especially for the hydrodesulphurising of condensed hydrocarbon fractions.

The invention is also directed to an additive for improving the octane number and the volatility properties (front end volatility) of gasolines which additive is characterised by having a content of 60 to 99.5% by weight, advantageously 97 to 99% by weight, of methyl tert.-butyl ether.

The invention is hereinafter more fully described by way of example by reference to the drawing, in which is represented the flow diagram of an installation by which the process of the invention may be carried into effect.

A mixture of light hydrocarbons, suitably a gas mixture which forms on separation by distillation from crude oil, is supplied through a pipe 1 to a rectifier column 2. The mixture is separated by distillation into a $C_{1-3}$ stream and a $C_{4+}$ stream. The $C_{1-3}$ stream leaving at the top serves as initial material for the methanol synthesis and is supplied by way of pipe 3 to the reforming stage of a methanol plant 27. The bottom fraction, consisting of $C_4$ and heavier hydrocarbons, passes through a pipe 4 to a column 5, in which the $C_4$ fraction is distilled off at the top and $C_5$ and higher hydrocarbons are removed as bottom product through a pipe 6. The $C_4$ fraction, which generally consists of butane, passes through a pipe 7 to the de-isobutanising column 8, in which is effected a separation of the total charge into isobutane and n-butane. The n-butane is extracted as bottom product through a pipe 9 and supplied to a catalytic isomerisation reactor 10, in which the n-butane is partially changed to isobutane. The mixture of isobutane and n-butane is removed from the reactor 10 by way of pipe 11 and, after separation of lighter hydrocarbons in a column (not shown), is again supplied to the de-isobutanisation column 8.

The high-percentage isobutane is heated in the heat exchanger 13 and, after expansion and being combined with isobutane returned by way of pipe 35, is supplied to one of the catalytic dehydrogenation reactors 14a or 14b. The two reactors 14a, 14b are alternately charged with the stream of isobutane, the reactor switched off at any time being regenerated with hot air. The exhaust gas of the dehydrogenation reactor consists essentially of an isobutene/isobutane mixture and passes by way of pipe 15 to a quenching tower 16, in which it is quenched by direct contact with cold oil. The mixture then flows through a pipe 17 to a multi-stage compressor 18 with intermediate cooling, by which the pressure is for example raised to 10 atmospheres. The gas mixture then passes through a pipe 19 into an absorption column 20, in which isobutene and isobutane are washed out of the gas stream with absorption oil. Hydrogen, and light hydrocarbons formed as secondary product of the dehydrogenation, remain in the gas phase and leave the installation through pipe 21. The hydrogen can be recovered from this secondary product and can, for example, be used in connection with the isomerisation and/or with the hydrodesulphurisation of condensed hydrocarbons. The cold absorption oil, charged with $C_4$ hydrocarbons, passes through a pipe 22 into the desorbing unit 24, in which the $C_4$ hydrocarbons are driven off by heating the absorption solution. The regenerated absorption oil flows back by way of pipe 23 to the absorber 20. The gas mixture, consisting essentially of isobutene and isobutane, leaves the desorbing unit by way of pipe 25.

The isobutene/isobutane mixture as thus obtained is fed, together with methanol introduced by way of a pipe 28 from the methanol plant 27 and methanol/ether mixture returned by way of pipe 33, and after preheating (not shown) into the catalytic etherifying reactor 26. The reactor 26 contains a solid bed catalyst and is provided with an internal cooling system (not shown). In the reactor, the isobutene introduced by way of pipe 25 is reacted with methanol to form methyl tert.-butyl ether. A mixture consisting substantially of methyl tert.-butyl ether, isobutane and excess methanol leaves the reactor 26 and is supplied through a pipe 29 to a first pressure column 30. In the column 30, the isobutane is distilled at the top and is combined by way of a pipe 35 with the charging flow for the dehydrogenation reactors 14a, 14b. The sump product of the column 30 is a mixture of methyl tert.-butyl ether and methanol and is supplied by way of pipe 31 to a second pressure column 32, in which an azeotrope consisting of methanol and methyl tert.-butyl ether is distilled at the top end, this mixture being returned by way of pipe 33 into the etherification reactor 26. The methyl tert.-butyl ether is extracted as product from the sump of the column 32 at 34.

EXAMPLE

A desulphurised stream of liquid gas, resulting from the processing of petroleum or from a petroleum gas reservoir, is processed in an installation corresponding substantially to the installation which is shown in the drawing, the said stream consisting substantially of 14 parts by weight of $C_1$–$C_3$ hydrocarbons, 44 parts by weight of $C_4$ hydrocarbons (essentially n-butane and isobutane; 60–99% $nC_4$ and 1–40% $iC_4$) and 22 parts by weight of $C_5$ and higher hydrocarbons. In the distillation column 2, the liquid stream is separated into 15 parts by weight of $C_1$–$C_3$ hydrocarbons with a low butane content and into $C_4$ and higher hydrocarbons. The $C_1$–$C_3$ hydrocarbons are converted by reforming with steam and low-pressure synthesis to 18 parts by weight of methanol. The $C_{4+}$ hydrocarbons are split up in column 5 into 22 parts by weight of $C_{5+}$ hydrocarbons as bottom product, which can for example be used, inter alia, for admixture with benzene, production of petrochemicals, etc. and 43 parts by weight of top product, consisting essentially of n-butane and some isobutane. The top or head product is supplied to the de-isobutanisation column, 8, which is combined with a catalytic isomerisation plant for isomerising n-butane to isobutane. The isomerisation reactor 10 is operated at 170° C., a pressure of 20 atmospheres, an hourly liquid space velocity of 4 $h^{-1}$ and with a molar ratio of hydrogen to charging liquid of 0.3:1. Supplied to the isomerisation reactor is 1 part by weight of gas with 80% hydrogen (secondary product of the dehydrogenation or methanol synthesis), together with return hydrogen. For the purpose of removing propane and lighter gases, the isomer is stabilised and is then split up, as a result of which there are obtained 42 parts by weight of 98 to 99% isobutane and also an n-butane fraction with small quantities of $C_{5+}$ hydrocarbons.

This isobutane product is supplied to the dehydrogenation reactors 14, possibly together with 28 parts by weight of returned raffinate from the etherification stage, after it has been heated in the preheater 13. The dehydrogenation takes place in a cyclic, adiabatic, catalytic solid bed process with three or more reactors. The heat of reaction necessary for the 10-minute dehydrogenation periods is substantially equal to the heat of combustion of the coke deposited on the catalyst, which heat is generated during the catalyst regeneration with preheated air. The entire period for reaction, flushing and regeneration is 20 minutes. The catalyst is chromium oxide in an amount of 18 to 20% on aluminium oxide with admixed inert particles of high heat capacity, so as to achieve the necessary heat capacity of the bed. The dehydrogenation takes place at 540° C., a pressure of 300 mmHg absolute and an hourly space velocity of the liquid of 2.5. The yield of isobutene from isobutane amounts to 75%. The dehydrogenation product from the reactors is quenched by direct contact with circulating oil and is compressed in the compressor unit 18 to 12 atmospheres. The total dehydrogenation product, in an amount of 70 parts by weight, is then split up by absorption and desorption and the liquid as thereby recovered is stabilised for the removal of propane and lighter gases. There are obtained 59 parts by weight of a mixture which consists of at least 97% of isobutene and isobutane in the molar ratio of 15:1, and also a small quantity of n-butane, other butenes and traces of higher hydrocarbons. In addition, there are formed 9 parts by weight of propane and lighter gases, including hydrogen. The $C_{5+}$ hydrocarbons and losses amount to 2 parts by weight. Eighteen parts by weight of methanol are mixed with 59 parts by weight of isobutene/isobutane and possibly with unreacted methanol from column 32 and supplied to the etherification reactor 26. The etherification occurs at about 60° C. in the liquid phase on a sulphonated, strongly acid, macroporous, organic ion exchange resin with a molar ratio between methanol and isobutene in the range from 1:1 to 2:1, advantageously 1.2:1 to 1.5:1. The etherified mixture is split up in the de-butanising column 30 into 28 parts by weight of isobutane, with a small content of other unreacted hydrocarbons, as top product, and into a bottom product, which is separated by distillation in the column 32 into 49 parts by weight of methyl tert.-butyl ether and unreacted methanol. The methyl tert.-butyl ether product contains about 98% of methyl tert.-butyl ether, 1.0% of methanol and 1.0% of other compounds.

The methyl tert.-butyl ether product as produced has the following mixing or blending properties: 110 to 135 RON and 98 to 110 MON, depending on the nature of the gasoline components.

The product mixture of methanol, methyl tert.-butyl ether and unreacted hydrocarbon can also be directly admixed with a large quantity of gasoline, without hydrocarbons and methanol having to be separated out beforehand. The concentration of the methyl tert.-butyl ether in the mixture is then in the region of 60%. This methyl tert.-butyl ether product of low concentration is added to the gasoline in the amount as permitted by the volatility properties and the required behaviour of the gasoline.

What is claimed is:

1. In a process for the production of methyl tert.-butyl ether from a mixture of light hydrocarbons containing butane or butanes, whereby (i) the butane fraction is separated from the mixture, (ii) n-butane of the butane fraction is isomerised to form isobutane, (iii) the isobutane is dehydrogenated to form a dehydrogenation mixture having an isobutene/isobutane molar ratio in the range from 0.4 to 2:1, (iv) isobutene contained in the dehydrogenation mixture is etherified with methanol to form methyl tert.-butyl ether, and (v) the isobutane from the etherification mixture is separated and recycled to the dehydrogenation step; the improvement which comprises:

(a) separating the butane fraction and the isomate obtained with the isomerisation of the n-butane into an n-butane fraction and an isobutane fraction by means of distillation;
    (b) passing the resulting n-butane fraction to the isomerisation step;
    (c) dehydrogenating the resulting isobutane fraction which, together with said isobutane separated and recycled from the etherification mixture, has an isobutane content of from about 70% to 100% by weight, to thereby form the dehydrogenation mixture;
    (d) separating from the resulting dehydrogenation mixture a mixture consisting essentially of all the isobutane and isobutene, by means of absorption and desorption separation techniques, which separated isobutene/isobutane mixture is thereafter reacted with methanol to form the etherification mixture comprising methyl tert.-butyl ether and isobutane; and
    (e) thereafter separating substantially all of the isobutane from the etherification mixture by distillation, which isobutane is recycled to the dehydrogenation step.

2. A process according to claim 1 wherein after the separation of isobutane, unreacted methanol is separated from the etherification mixture by distillation.

3. A process according to claim 1, wherein after the distillation of isobutane, unreacted methanol is distilled off as methanol/methyl tert.-butyl ether azeotrope from the residual etherification mixture consisting of methyl tert.-butyl ether and methanol and the azeotrope is returned to the etherification stage.

4. A process according to claim 1, 2 or 3, wherein the dehydrogenation is operated with a charge of such a composition and under such reaction conditions that the butadiene content of the dehydrogenation mixture amounts to less than 0.5% by weight.

5. A process according to claim 4 wherein the isobutene/isobutane mixture is etherified with methanol prepared by reforming of light hydrocarbons with steam and catalytic synthesis under a pressure in the range from about 40 to 100 atmospheres.

6. A process according to claim 1, 2 or 3, wherein hydrogen is separated from the product gas of the dehydrogenation and/or the process gas and/or the waste gas of the methanol synthesis and this hydrogen is used with the isomerisation step.

7. A process according to claim 1, 2 or 3, wherein the isobutane is dehydrogenated to an isobutene/isobutane molar ratio in the range from 1.0 to 1.5:1.

8. A process according to claim 7 wherein the isobutane fraction which is dehydrogenated has a content of about 90 to 99% by weight isobutane.

* * * * *